(12) United States Patent
Lehmann et al.

(10) Patent No.: US 8,329,104 B2
(45) Date of Patent: Dec. 11, 2012

(54) MEASUREMENT DEVICE WITH AT LEAST ONE SENSOR

(75) Inventors: Mirko Lehmann, Ebnat-Kappel (CH); Ingo Freund, Freiburg (DE); Sonja Mohry, Freiburg (DE); Holger Klapproth, Freiburg (DE)

(73) Assignees: Micronas GmbH, Freiburg I.Br. (DE); Micronas Holding GmbH, Freiburg I. Br. (DE)

( * ) Notice: Subject to any disclaimer, the term of this patent is extended or adjusted under 35 U.S.C. 154(b) by 957 days.

(21) Appl. No.: 12/146,644

(22) Filed: Jun. 26, 2008

(65) Prior Publication Data

US 2009/0175764 A1 Jul. 9, 2009

(30) Foreign Application Priority Data

Jul. 4, 2007 (EP) ..................... 07013079

(51) Int. Cl.
*G01N 15/06* (2006.01)
*G01N 33/00* (2006.01)
*G01N 33/48* (2006.01)
*C12Q 1/00* (2006.01)
*G01N 33/53* (2006.01)
*G01N 33/566* (2006.01)
*G01N 33/543* (2006.01)

(52) U.S. Cl. ............ 422/68.1; 435/4; 435/7.1; 436/501; 436/518

(58) Field of Classification Search ................ 422/68.1
See application file for complete search history.

(56) References Cited

U.S. PATENT DOCUMENTS

| 5,017,340 | A | * | 5/1991 | Pribat et al. ..................... 422/98 |
| 5,730,942 | A | * | 3/1998 | Megerle et al. ............ 422/82.01 |
| 6,922,081 | B2 | | 7/2005 | Frey et al. |
| 7,598,044 | B2 | * | 10/2009 | Klapproth ..................... 435/7.1 |
| 2004/0041717 | A1 | | 3/2004 | Frey et al. |
| 2004/0249227 | A1 | * | 12/2004 | Klapproth et al. ............ 585/250 |
| 2006/0127716 | A1 | | 6/2006 | Lehmann |
| 2006/0155511 | A1 | | 7/2006 | Steinmueller et al. |
| 2006/0172928 | A1 | | 8/2006 | Klapproth |
| 2006/0223103 | A1 | * | 10/2006 | Klapproth ....................... 435/6 |
| 2006/0281435 | A1 | | 12/2006 | Shearer et al. |
| 2008/0040041 | A1 | | 2/2008 | Kilgus |

FOREIGN PATENT DOCUMENTS

| DE | 3243540 A1 | 5/1984 |
| DE | 3440207 A1 | 5/1985 |
| DE | 3341597 A1 | 4/1986 |
| DE | 3809107 A1 | 9/1989 |
| DE | 4341597 A1 | 6/1995 |

(Continued)

*Primary Examiner* — In Suk Bullock
*Assistant Examiner* — Bryan Kilpatrick
(74) *Attorney, Agent, or Firm* — Muncy, Geissler, Olds & Lowe, PLLC

(57) ABSTRACT

A measurement device has at least one sensor for detecting a parameter, a data storage unit, and a power supply for said sensor and data storage unit. In addition to the first sensor, the measurement device has at least one second sensor connected to the power supply and to the data storage unit. The second sensor is provided for detecting a physical quantity acting on the first sensor and is capable of permanently altering the measurement characteristic of the first sensor. An evaluator functions coactively with the second sensor and the data storage unit so that the permanent alteration of the measurement characteristic of the first sensor is recordable as a function of the measurement signal of the second sensor.

19 Claims, 5 Drawing Sheets

FOREIGN PATENT DOCUMENTS

Figure 1:
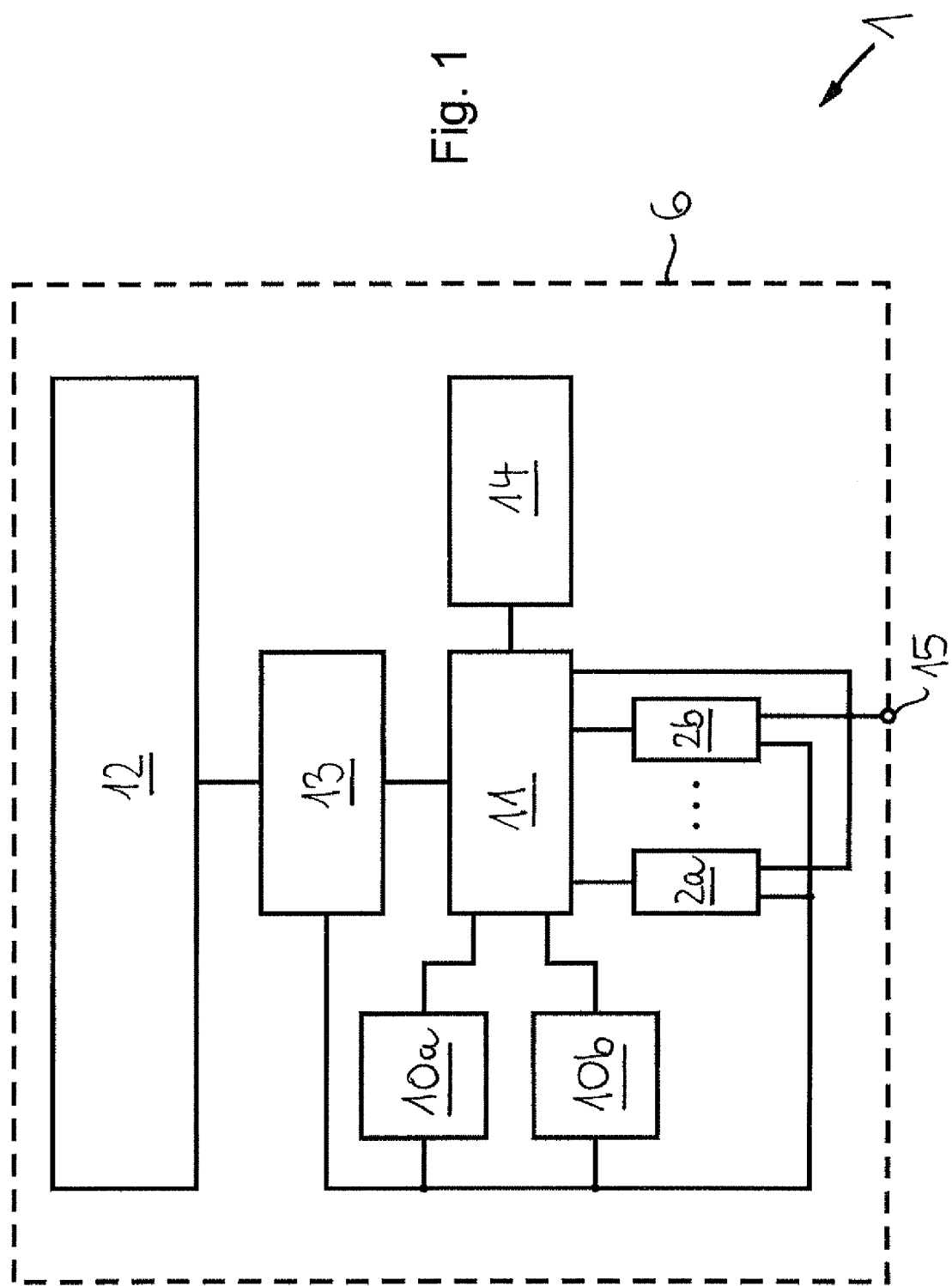

| | | |
|---|---|---|
| DE | 10064859 A1 | 7/2002 |
| DE | 10255736 A1 | 6/2004 |
| EP | 1534740 B1 | 12/2006 |
| WO | 0233397 A1 | 4/2002 |
| WO | 2004025223 A2 | 3/2004 |
| WO | 2006005093 A1 | 1/2006 |

* cited by examiner

MEASUREMENT DEVICE WITH AT LEAST ONE SENSOR

The invention relates to a measurement device with at least one sensor for detecting a parameter, with a data storage unit, and with a power supply for said sensor and data storage unit.

Such a measurement device is disclosed in US 2006/0281435 A1. It comprises an integrated circuit connected to a data storage unit, a biological sensor, and a power supply which has means for generating electrical energy from an electromagnetic field residing in the vicinity of the measurement device. The integrated circuit and the data storage unit are constantly supplied with electrical energy via the power supply practically over the entire service life of the measurement device. The measurement device is thus capable of operation without an external power cable. However, a disadvantage resides in the measurement device in that the measurement characteristics of the biological sensor are subject to an aging process and thus—in terms of the service life of the sensor—correspondingly large tolerances. The measurement signal is thus encumbered with a relatively large measurement error.

DE 38 09 107 A1 also discloses a measurement device of the aforementioned nature, which comprises a gas sensor whose measurement characteristic is influenced by a plurality of parameters such as temperature, humidity, and pressure and must be recalibrated periodically. To this end, the sensor is stimulated during testing times by means of an electrical impulse imprinted in its measuring circuit for generation of its own electrical impulse, whose form is compared with that of the imprinted electrical impulse. The current parameters of the sensor are derived from this comparison and filed in a data storage unit. A disadvantage resides in the measurement device in that it cannot be used to measure the gas concentration during the testing times. Furthermore, the method disclosed in DE 38 09 107 A1 is only suitable for sensors in which the internal electrical resistance changes under the influence of physical quantities.

The object of the invention is therefore to design a measurement device of the aforementioned nature which enables an alteration of the measurement characteristic of the sensor to be recorded.

This object is achieved in that the measurement device has, in addition to the first sensor, at least one second sensor connected to the power supply and the data storage unit, said second sensor being provided for the detection of a physical quantity acting on the first sensor and capable of permanently altering the measurement characteristic of said first sensor, and further achieved in that an evaluator functions coactively with the second sensor and the data storage unit so that the permanent alteration of the measurement characteristic of the first sensor is recordable as a function of the measurement signal of the second sensor. A permanent alteration is to be understood as one in which the alteration of the measurement characteristic of the first sensor persists, at least partially and particularly irreversibly, even after elimination of the influence of the physical quantity thereon.

The invention is based on the finding that a permanent alteration of the measurement characteristic of a sensor is essentially due to the action of one or a plurality of physical quantities on the sensor, and that the alteration of the measurement characteristic can be determined by on-going measurement of this quantity/these quantities by means of at least one second sensor and analysis of its measurement signal (measurement signals). The on-going measurement can be a continuous measurement or a discontinuous measurement. For the latter, preference is given to selection of a sufficiently short interval between two sequential measurement times so that no change or only a minor change of the physical parameter(s) takes place within the time interval. By means of the evaluator, the alteration of the measurement characteristic of the first sensor caused by the physical quantity(ies) is detected and filed in the data storage unit. The data storage unit can thus have a minimum capacity of only one bit if binary information is filed in the data storage unit indicating whether or not the measurement characteristic of the first sensor falls within a prespecified alteration range. Preference is given, however, to the data storage unit having a larger storage capacity so that upon detection of an alteration in the measurement characteristic of the first sensor, this alteration can be filed with correspondingly greater precision in the data storage unit. Instead of a parameter for the alteration of the measurement characteristic, it is obviously also possible to file the measurement signal of the second sensor directly in the data storage unit and then detect, by means of the evaluator, the alteration of the measurement characteristic of the first sensor from the temporal progression of the filed measurement signal.

In a preferred embodiment of the invention, parameters are filed in the data storage unit which have combinations of values that always comprise at least one measurement signal value or a range of measurement signal values of the second sensor and a value for the alteration of the measurement characteristics of sensor, wherein the evaluator for detecting the alteration of the measurement characteristic of the first sensor caused by the action of the physical quantity measurable with the second sensor is connected to the data storage unit. The alteration of the measurement characteristic of the first sensor can be determined with great accuracy by means of the parameters.

It is advantageous if the measurement device has a timer for detecting the age of the first sensor, if the parameters include combinations of values for at least two different age ranges of the first sensor, and if the combinations of values allocated to the age ranges are retrievable from the data storage unit as a function of a time measurement signal of the timer. In the analysis of the measurement signal of at least the one second sensor, the sensitivity of the first sensor as a function of the age of said first sensor can then be taken into account with respect to the physical quantity measurable with the second sensor. The influence of the physical parameter may thus reduce or increase the measurement sensitivity of the first sensor, depending on the age of the latter.

The parameters are advantageously filed in the data storage unit in the form of at least one response curve and/or at least one grid. The at least one response curve can be a line and/or have a progressive and/or degressive gradient or segment. The response curve can also be an $n^{th}$ degree polynomial, wherein n is a positive integer. It is also possible for the response curve to be a logarithmic or exponential curve. The grid can be filed in the data storage unit in the form of sampling points. Intermediate points can be interpolated from the sampling points as needed by means of the evaluator.

In a preferred embodiment of the invention, the evaluator has an integration element for forming an integration signal from the measurement signal of the second sensor, wherein the evaluator is configured to record the alteration of the measurement characteristic of the first sensor as a function of the integration signal. By means of the integration mechanism, the time period that the physical quantity has been acting on the first sensor and the amplitude of the measurement signal of the physical quantity can be taken into account in determining the alteration of the measurement characteristic of the first sensor caused by the action of at least the one physical quantity thereon.

If the first sensor for detection of the parameter comprises biological material, it is advantageous if the integration mechanism has a non-linear, preferably progressive, and particularly logarithmic characteristic. The sensitivity of the biological material, which decreases more or less logarithmically with the integral of the physical quantity under the action of the physical quantity on said biological material, can thus be taken into account in the determination of the alteration of the measurement characteristic of the first sensor.

In an advantageous embodiment of the invention, the measurement device has at least one multiplication element comprising a first multiplication input connected to the measurement signal output of the second sensor or to a connector for the integration signal and a second multiplication input connected to the data storage unit. The measurement signal of the second sensor can then be weighted, prior to its integration, with the factors dependent on the amplitude of the measurement signal filed in the data storage unit. The factors can also be selected as a function of at least one other measurement signal, e.g., for a more precise determination of a permanent or irreversible alteration of the measurement characteristic caused by a plurality of different physical quantities acting simultaneously on the first sensor. The multiplication element can also be integrated in a microcomputer on which a suitable operating program can be run.

It is especially advantageous if the measurement device has at least one adjustment mechanism for at least the first sensor, by means of which the measurement characteristic of the first sensor is adjustable, and if the evaluator is control-connected to the adjustment mechanism in such a way that, when an alteration of the measurement characteristic of the first sensor is recorded, the evaluator can be adjusted by means of the adjustment mechanism to compensate for this alteration. In this manner it is possible to compensate, at least partially, for the permanent alteration of the measurement characteristic of the first sensor caused by the action of the physical quantity (ies).

In a preferred embodiment of the invention, the at least one first sensor is a biochip, which has a substrate on which at least one receptor is immobilized on at least one test site, said receptor being bond-specific for a ligand to be detected. Said receptor can include a nucleic acid or a derivative thereof (DNA, RNA, PNA, LNA, oligonucleotides, plasmids, chromosomes), a peptide, protein (enzyme, protein, oligopeptides, cellular receptor proteins and complexes thereof, peptide hormones, antibodies and fragments thereof), carbohydrates and their derivatives, particularly a glycosylated protein and glycoside, fat, fatty acid, and/or lipid.

In such a measurement device, the at least one second sensor advantageously includes at least one temperature, humidity, and/or radiation sensor. It is thus possible to take into account the determining factors essential for the alteration of the measurement characteristic of the biochip, namely the temperature, the humidity, and the light or the brightness in the vicinity of the receptors, in the detection of the alteration of the measurement characteristic and, if applicable, the compensation thereof.

It is advantageous if the at least one receptor is immobilized in stabilized form on the substrate. The service life of the receptors is improved thereby. Furthermore, the temperature range to which the receptors may be exposed without the measurement characteristic of the first sensor comprising the receptors undergoing substantial alteration is expanded. A monitoring of the at least one physical quantity capable of permanently altering the measurement characteristic of the first sensor is therefore of particular importance in this case. The receptors can be stabilized during the manufacture of the biochip, particularly by coating the receptor immobilized on the substrate with a compound that includes at least one unreduced disaccharide and at least one LEA-class protein or polypeptide. Suitable disaccharides and proteins are disclosed in EP 1 534 740 B1.

The biochip advantageously has at least two test sites which are preferably laterally separated from each other and on which a first sensor is always arranged, wherein at least one parameter is always filed in the data storage unit for each of these test sites. The varying alteration of the receptors under the action of heat and/or cold can thus be taken into account. For example, it may be that a first receptor arranged on a first test site shows a larger measurement signal after a temperature effect and a second receptor arranged on a second test site shows a smaller measurement signal prior to the temperature effect. By means of the parameters for the individual test sites filed separately in the data storage unit, it is also possible to take into account that different antibodies serving as receptors on the individual test sites can have different decomposition sequences.

In an advantageous embodiment of the invention, the substrate is a semiconductor chip in which at least one sensor element whose measurement signal is dependent on the binding of the ligand is integrated. The sensor element can be an optical sensor for detecting luminescent radiation generated as a function of the binding of the ligand to the receptor and/or an ion-sensitive field effect transistor (ISFET).

The power supply provided at least for the second sensor and the data storage unit can comprise an electrical energy source, particularly a battery and/or a fuel cell. It is even possible for the fuel cell to be integrated in the semiconductor chip, thus assuring that the first sensor is monitored for the effect of the physical quantity(ies) from the time it is manufactured. Furthermore, the fuel cell integrated in the semiconductor chip enables a simple, cost effective, and compact construction of the measurement device. The fuel cell can particularly comprise the characteristics disclosed in DE 102 55 736 A1.

In another advantageous embodiment of the invention, the power supply has a mechanism for generating electrical energy from optical radiation, from electromagnetic radiation, and/or from mechanical kinetic energy. Preference is given to the integration of this mechanism in the semiconductor chip with semiconductor manufacturing and/or microsystems technology methods. It can particularly include a photocell, means for converting radio waves into direct current voltage, and/or a piezoelectric converter.

Figure 2:
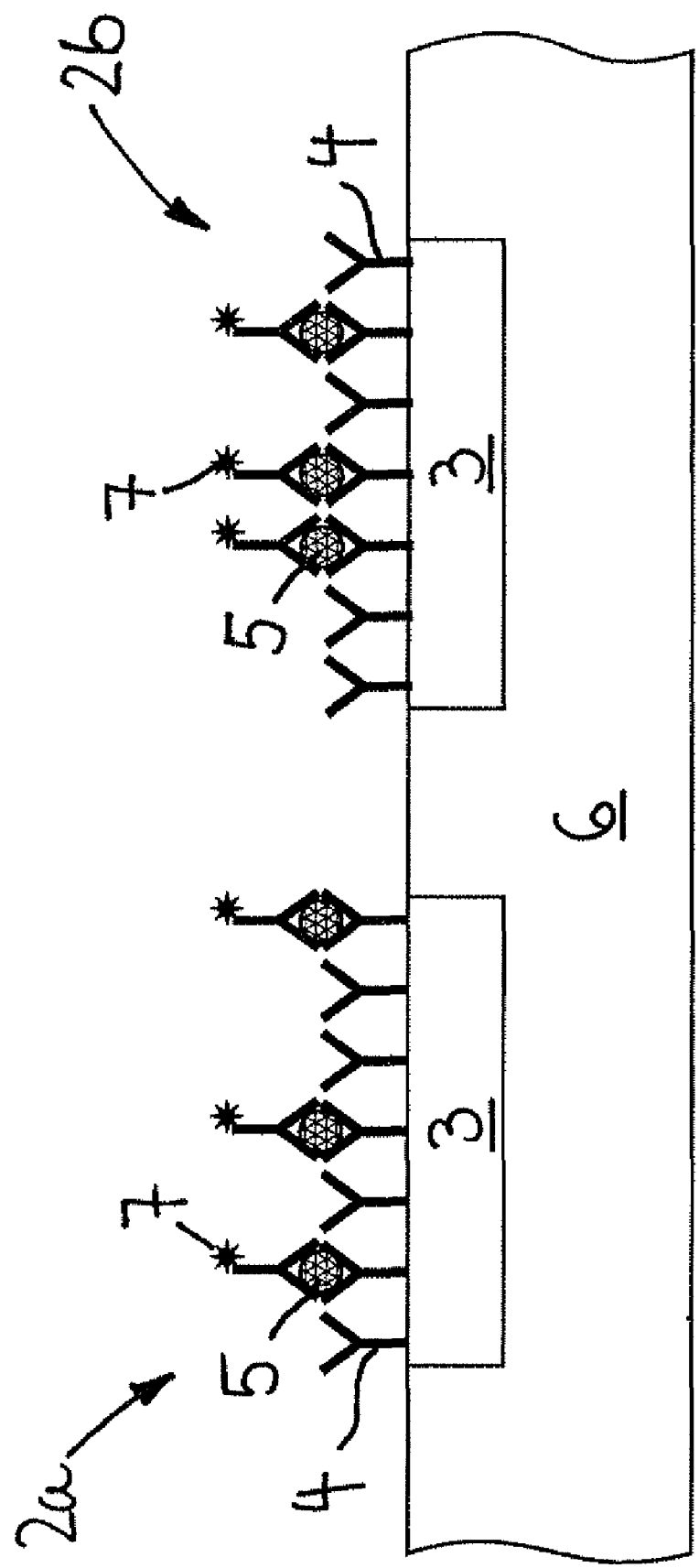
Figure 3:
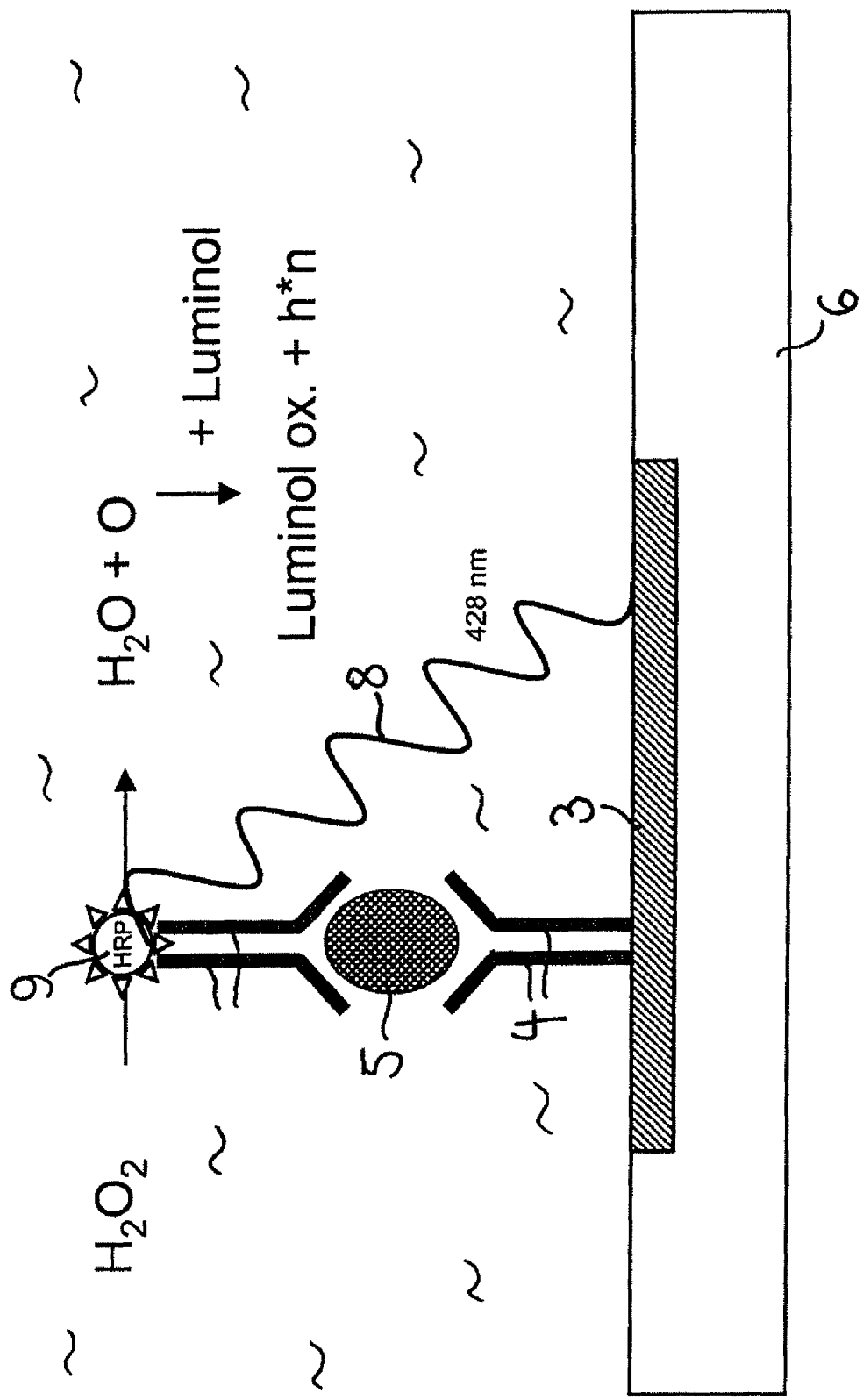
Figure 4:
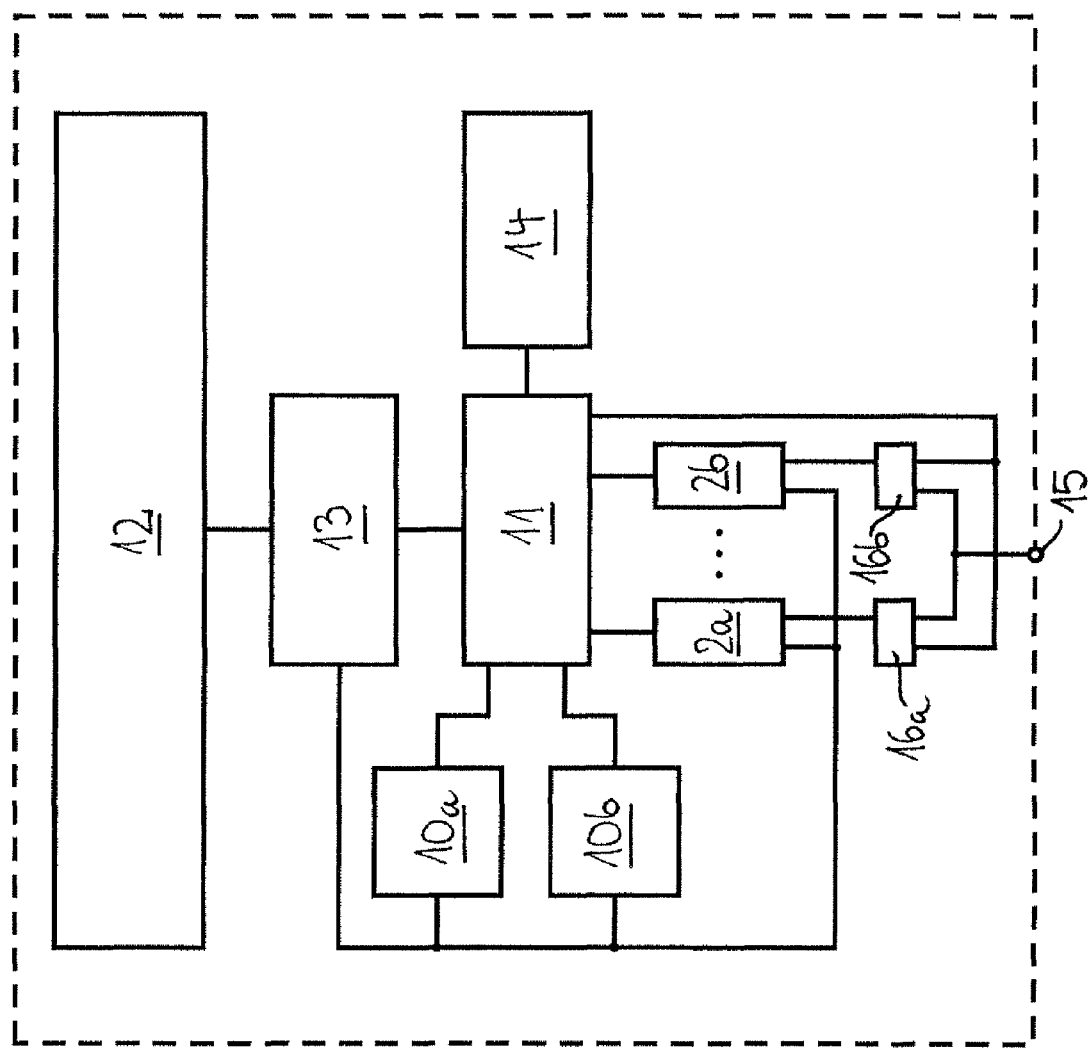
Figure 5:
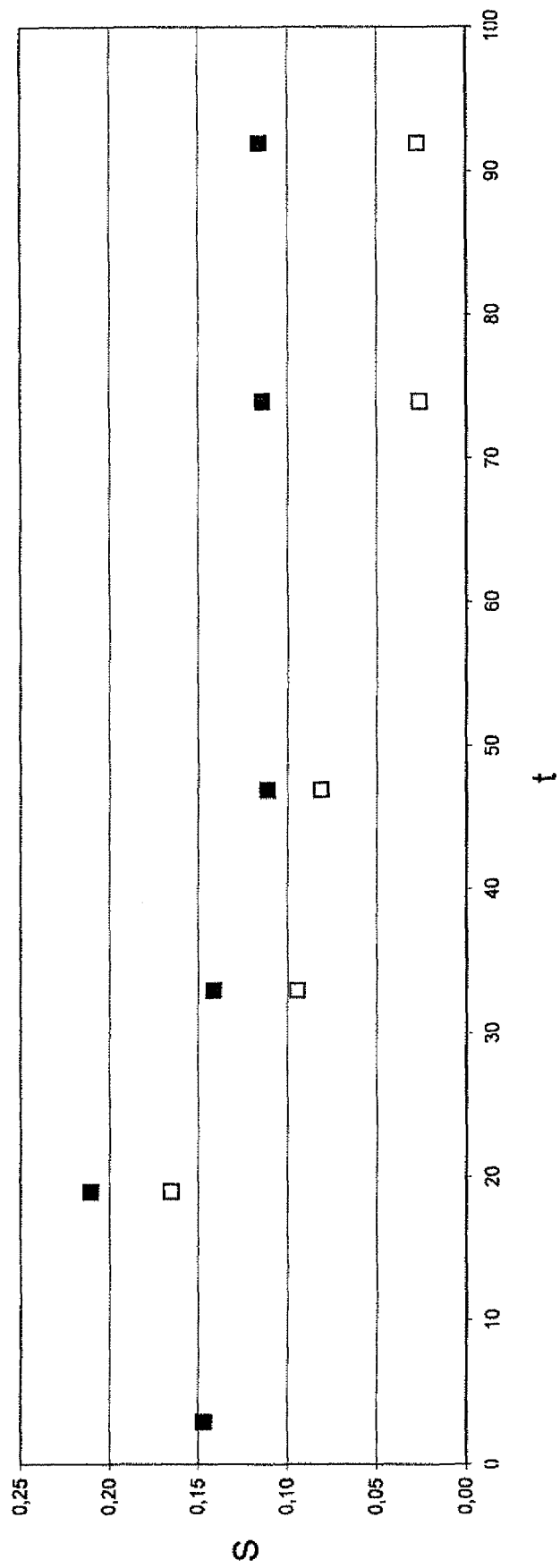

Illustrative embodiments of the invention are explained in detail with reference to the drawing. Shown are:

FIG. 1 a block diagram of a first illustrative embodiment of a measurement device comprising a plurality of first and second sensors arranged in matrix form, FIG. 2 a partial cross-section of the measurement device, wherein two first sensors are discernible on which luminescent radiation is generated as a function of the binding of a ligand to a receptor, FIG. 3 a partial cross-section of a measurement device in which the luminescent radiation is chemically generated, FIG. 4 a block diagram of a second illustrative embodiment of the measurement device, FIG. 5 a schematic illustration of the light density signal of an optical radiation, which is generated as a function of the binding of a ligand to a receptor of a biochip immobilized on a substrate, wherein the storage life t of the biochip at a predefined constant temperature is plotted on the abscissa and the light density signal S is plotted on the ordinate, wherein the open squares indicate measurement points of a biochip with an unstabilized receptor and the solid squares indicate measurement points of a biochip with a stabilized receptor.

A measurement device designated in its entirety by 1 in FIG. 1 has a plurality of first sensors 2a, 2b, which always have an optical sensor element 3 and at least one receptor 4 allocated thereto which is bond-specific for a specific ligand 5 to be detected and/or whose concentration is to be determined in an analyte.

As can be discerned in FIG. 2, the receptors 4 are immobilized on test sites which are arranged on a planar substrate 6. The receptors 4 of at least two test sites are bond-specific for different ligands 5. The individual test sites are separated from each other by receptor-free zones.

For analysis purposes, the analyte is brought into contact with the test sites in such a way that the ligands 5 contained therein have the opportunity to bond specifically to the receptors 4. The ligands 5 are marked with a marker 7, which is stimulated with excitation radiation to emit luminescent radiation 8. The wavelength of the luminescent radiation 8 is different from that of the excitation radiation.

It can be discerned in FIG. 2 that the sensor element 3 is always directly arranged underneath the at least one receptor 4 allocated thereto and integrated in the substrate 6 that is configured, at least in certain sections, as a semiconductor chip. The sensor elements 3 are insensitive to the luminescent radiation 8 emitted by the markers 7 and to the excitation radiation.

In the illustrative embodiment illustrated in FIG. 3, the luminescent radiation 8 is chemically generated as a function of the binding of the ligand 5 to the receptor 4. The ligand 5 is marked with an enzyme 9. Luminol and hydrogen peroxide are added to the analyte. In the absence of the enzyme 9, a chemical reaction between the luminol and the hydrogen peroxide takes place in which the luminol emits luminescent radiation 8 as it is oxidized. As in the illustrative embodiment shown in FIG. 2, in FIG. 3 the sensor element 3 sensitive to the luminescent radiation 8 is also arranged directly underneath of the at least one receptor 4.

In addition to the first sensors 2a, 2b, the measurement device has second sensors 10a, 10b which are provided for the detection of physical quantities acting on the first sensors 2a, 2b and capable of permanently altering the measurement characteristic of said first sensor 2a, 2b. A first second sensor 10a is configured as a temperature sensor and another second sensor 10b is configured as a humidity sensor. The second sensors 10a, 10b are also integrated in the substrate 6.

An evaluator 11 having inputs connected to measurement signal outputs of the second sensors 10a, 10b is provided for the determination of a permanent alteration of the measurement characteristic of at least a first sensor 2a, 2b caused by the action of the aforementioned physical quantities. The evaluator 11 has a microprocessor not shown in any greater detail in the drawing which is controlled by an operating program filed in a program memory. A timer 13 is integrated in the substrate 6 for measuring the age of the first sensors 2a, 2b.

A data storage unit 14, which is connected via an electronic bus to the evaluator 11, is provided in addition to the program memory. Furthermore, the data storage unit 14 is connected to the second sensors 10a, 10b via the evaluator 11. Parameters are always filed in the data storage unit for each first sensor 2a, 2b, said parameters having combinations of values which always allocate a value for the alteration of the measurement characteristic of the respective first sensor 2a, 2b to measurement signal values or ranges of measurement signal values of the second sensors 10a, 10b for different age ranges of the first sensors 2a, 2b.

A power supply 12 for supplying the first sensors 2a, 2b, the second sensors 10a, 10b, the evaluator 11, and the data storage unit 14 with electrical energy is integrated in the substrate, configured as a fuel cell, and connected via electric lines not shown in any greater detail in the drawing to the sensors 2a, 2b, 10a, 10b, the evaluator 11, the timer 13, and the data storage unit 14.

In addition, the timer 13 is connected to the power supply 12 and initiates measurement cycles in prespecified time intervals in which at least one measurement value is detected by means of each second sensor 10a, 10b and transmitted to the evaluator 11. For each first sensor 2a, 2b, the value for the alteration of the measurement characteristic of the respective first sensor 2a, 2b allocated to the respective measurement values is always read out from the data storage unit 14. The values always thus obtained for each first sensor 2a, 2b are integrated in the evaluator 11 in order to determine a status value. The status values are filed in the data storage unit 14. They can be read out from the measurement device 1 via an electrical connector 15 connected to the data storage unit 14, in order to retrieve the current measurement characteristic of each of the first sensors 2a, 2b and/or to check whether the individual first sensors 2a, 2b are still usable for a measurement. For readout of the measurement signals from the first sensors 2a, 2b, the latter are also connected to the connector 15.

In the illustrative embodiment shown in FIG. 4, the measurement device 1 always has an adjustment mechanism 16a, 16b for each first sensor 2a, 2b, by means of which the measurement characteristic of the respective first sensor 2a, 2b is adjustable. The adjustment mechanism 16a, 16b can have, for example, a controllable amplifier and/or attenuator arranged between the measurement signal output of the respective first sensor 2a, 2b and the connector 15. The evaluator 11 is control-connected to the adjustment mechanisms 16a, 16b in such a way that when an alteration of the measurement characteristic of a first sensor 2a, 2b is recorded, the adjustment mechanism allocated to said sensor 2a, 2b is adjusted to compensate for the alteration.

Preference is given to immobilization of the receptors 4 in stabilized form on the substrate 6. The first sensors 2a, 2b will thus have a greater measurement sensitivity compared with a measurement device 1 in which the receptors 4 are not stabilized, especially after said measurement device 1 is stored for a prolonged period (FIG. 5).

The invention claimed is:

1. A measurement device comprising:
   at least one first sensor for detecting a parameter;
   a data storage unit and a power supply for supplying energy for said at least one sensor and for said data storage unit;
   at least one second sensor configured to detect a physical quantity acting on the at least one first sensor and for permanently altering a measurement characteristic of said first sensor based on a measurement signal from said at least one second sensor; and
   an evaluator connected to said at least one first sensor, to said at least one second sensor and to the data storage unit,
   wherein the permanent alteration of the measurement characteristic of the first sensor is recorded.

2. The measurement device as in claim 1, wherein parameters are filed in the data storage unit which comprise combinations of values which comprise at least one measurement signal value or a range of measurement signal values of the second sensor and a value for the alteration of the measurement characteristic of the first sensor, and wherein the evaluator for detecting the alteration of the measurement characteristic of the first sensor caused by the action of the physical quantity measurable with the second sensor is connected to the data storage unit.

3. The measurement device as in claim 1, further comprising a timer for detecting an age of the first sensor, wherein combinations of values for at least two different age ranges of the first sensor are stored in the data storage unit, and wherein the combinations of values allocated to the age ranges are retrievable from the data storage unit as a function of a time measurement signal of the timer.

4. The measurement device as in claim 2, wherein the parameters are filed in the data storage unit in the form of at least one response curve and/or at least one grid.

5. The measurement device as in claim 1, wherein the evaluator has an integration element for forming an integration signal from the measurement signal of the second sensor, and wherein the evaluator is configured so that it records the alteration of the measurement characteristic of the first sensor as a function of the integration signal.

6. The measurement device as in claim 5, wherein the integration signal has a nonlinear characteristic.

7. The measurement device as in claim 1, wherein it has at least one multiplication element comprising a first multiplication input connected to the measurement signal output of the second sensor or to a connector for the integration signal and a second multiplication input connected to the data storage unit.

8. The measurement device as in claim 1, further comprising at least one adjustment mechanism for at least the first sensor by means of which the measurement characteristic of said first sensor is adjustable, wherein the evaluator is control-connected to the adjustment mechanism in such a way that when an alteration of the measurement characteristic of the first sensor is recorded, said evaluator is adjusted by means of said adjustment mechanism to compensate for this alteration.

9. The measurement device as in claim 1, wherein the at least one second sensor includes at least one temperature, humidity, and/or radiation sensor.

10. The measurement device as in claim 1, wherein the at least one first sensor is a biochip comprising a substrate on which at least one receptor that is bond-specific for a ligand to be detected is immobilized on at least one test site.

11. The measurement device as in claim 10, wherein the at least one receptor is immobilized in stabilized form on the substrate.

12. The measurement device as in claim 10, wherein the biochip has at least two test sites on which a first sensor is always arranged, and further wherein at least one parameter for each of these test sites is always filed in the data storage unit.

13. The measurement device as in claim 10, wherein the substrate is a semiconductor chip in which at least one sensor element is integrated, whose measurement signal is dependent on the binding of the ligand to the receptor.

14. The measurement device as in claim 1, wherein the power supply has an electrical energy source.

15. The measurement device as in claim 1, wherein the power supply has a mechanism for generating electrical energy from optical radiation, from electromagnetic radiation, and/or from mechanical kinetic energy.

16. The measurement device as in claim 6, wherein the integration signal has a logarithmic characteristic.

17. The measurement device as in claim 12, wherein the at least two test sites are laterally separated from each other.

18. The measurement device as in claim 14, wherein the power supply includes a battery and/or a fuel cell.

19. A measurement device comprising:
a first sensor for detecting a parameter;
a data storage unit and a power supply for supplying energy for the first sensor and for the data storage unit;
a second sensor configured to detect a physical quantity acting on the first sensor and configured to permanently alter a measurement characteristic of the first sensor based on a measurement signal from the second sensor; and
an evaluator connectable to the first sensor, to the second sensor and to the data storage unit,
wherein the evaluator has an integration device for providing an integration signal based on the measurement signal from the second sensor, and
wherein the evaluator is configured such that it records the change in the measurement characteristic of the first sensor based on the integration signal.

* * * * *